US010751068B2

(12) United States Patent
Lynch et al.

(10) Patent No.: US 10,751,068 B2
(45) Date of Patent: Aug. 25, 2020

(54) INTRAMEDULLARY AUTOGRAFT HARVESTER (71) Applicant: Stryker European Holdings I, LLC, Kalamazoo, MI (US)

(72) Inventors: Robert Lynch, Portage, MI (US); Robin Büscher, Heikendorf (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 883 days.

(21) Appl. No.: 15/124,884

(22) PCT Filed: Mar. 10, 2015

(86) PCT No.: PCT/US2015/019680
§ 371 (c)(1),
(2) Date: Sep. 9, 2016

(87) PCT Pub. No.: WO2015/138432
PCT Pub. Date: Sep. 17, 2015

(65) Prior Publication Data
US 2017/0071610 A1 Mar. 16, 2017

Related U.S. Application Data (60) Provisional application No. 61/951,154, filed on Mar. 11, 2014.

(51) Int. Cl.
*A61B 17/16* (2006.01)
(52) U.S. Cl.
CPC ............... *A61B 17/1635* (2013.01)

(58) Field of Classification Search
CPC ........ A61B 17/32; A61B 2017/320024; A61B 2017/320028; A61B 2017/320032
See application file for complete search history.

(56) References Cited

U.S. PATENT DOCUMENTS

| 5,591,187 A | 1/1997 | Dekel |
| 6,695,859 B1 * | 2/2004 | Golden .............. A61B 17/0057 606/153 |
| 8,007,506 B2 * | 8/2011 | To ..................... A61B 17/32075 606/159 |
| 2011/0087257 A1 | 4/2011 | To et al. |

FOREIGN PATENT DOCUMENTS

WO 2012112579 A1 8/2012

OTHER PUBLICATIONS

International Search Report for Application No. PCT/US2015/019680 dated Jun. 17, 2015.

\* cited by examiner

*Primary Examiner* — Anu Ramana
(74) *Attorney, Agent, or Firm* — Lerner, David, Littenberg, Krumholz & Mentlik, LLP (57) ABSTRACT An intramedullary autograft harvesting instrument (100) includes a cutting rod (10) having a body (13) and a cutting head (14), a harvesting member (20) configured to be disposed about the body (13) of the cutting rod (10), and an outer tube (30) configured to be disposed about the harvesting member (20). A method of using the instrument (100) transports harvested tissue from an intramedullary canal.

17 Claims, 5 Drawing Sheets

INTRAMEDULLARY AUTOGRAFT HARVESTER

CROSS-REFERENCE TO RELATED APPLICATIONS

The present application is a national phase entry under 35 U.S.C. § 371 of International Application No. PCT/US2015/019680, filed Mar. 10, 2015, published in English, which claims the benefit of the filing date of U.S. Provisional Application No. 61/951,154, filed Mar. 11, 2014, entitled INTRAMEDULLARY AUTOGRAFT HARVESTER, the disclosures of which are hereby incorporated herein by reference.

BACKGROUND OF THE INVENTION

The inventions described herein generally relate to devices and methods for harvesting autograft tissue. More particularly, the inventions described herein relate to a flexible intramedullary autograft harvesting instrument and methods of using same.

Certain surgical procedures benefit from the use of harvested autograft tissue in other areas of the patient where bone growth is desired. Autograft tissue contains oseogenic tissue that has been shown to aid the development of hard osseous tissue. The autograft tissue can be placed in areas deemed appropriate by health care providers, typically surgeons, where bone growth is desired. These areas can include non-union of bone, fresh fractures, and spinal fusions. Such autograft tissue can be cancellous bone tissue removed from the intramedullary canal of the femur and tibia.

Current devices that are utilized for harvesting autograft tissue from intramedullary canals can be powered or manual devices. The manual devices can be difficult to use and hard to manipulate down the long canal of the bone. Some powered instruments used for these procedures to harvest autograft tissue do not adequately address the delicate nature of the cancellous tissue and can potentially destroy cellular viability due to cutting head velocity and cutting head geometry. In addition, powered instruments often utilize saline irrigation as a medium to help remove dislodged cancellous tissue and transport the desired tissue to a receptacle. When saline is used during the harvesting process, the resulting harvest lacks structure needed for shaping and compacting the harvested tissue. Furthermore, the saline must be squeezed out of or otherwise removed from the harvested tissue, which adds time to the procedure and potentially causes further cell viability damage.

Thus, there is a need for a surgical instrument for removing cancellous bone tissue from the intramedullary canal of the femur and tibia and a method of using the instrument that improves efficiency, eliminates or reduces damage to cellular viability, does not require saline irrigation, and to eliminates or reduces secondary steps to obtain a viable autograft tissue harvest.

BRIEF SUMMARY OF THE INVENTION

A first aspect of the present invention is an intramedullary autograft harvesting instrument including a cutting rod having a body and a cutting head, a harvesting member configured to be disposed about the body of the cutting rod, and an outer tube configured to be disposed about the harvesting member.

In accordance with other embodiments of the first aspect, the diameter of the body of the cutting rod may be constant along its length. The cutting head may have an outer diameter that is larger than the diameter of the body. The diameter of the body of the cutting rod may vary along its length. The cutting head may be connected with the body at a distal end of the cutting rod. The cutting head of the cutting rod may be configured to direct harvested material in a direction from the distal end toward a proximal end of the cutting rod.

The cutting head may include helical threads. The cutting head and the body may be comprised of the same material. The cutting head may be comprised of one or more metals. The one or more metals may include titanium. The cutting rod may be cannulated along its length to define a bore extending through the body and the cutting head. A proximal end of the cutting rod may be configured to engage with a tool for rotating the cutting rod. The harvesting member may be tubular along its length to define a lumen. The lumen of the harvesting member may be configured to house the body of the cutting rod.

An outer surface of the harvesting member may be configured to transport harvested material away from a distal end of the cutting rod and in a proximal direction. The outer surface of the harvesting member may include one or more helical threads defining one or more helical channels therebetween. A width of one of the channels may be constant along its path. A width of one of the channels may vary along its path. A width of one of the channels may be different than a width of another of the channels. Outermost portions of the one or more helical threads may be disposed on an imaginary cylinder. An outer diameter of the one or more helical threads may be constant. The one or more helical channels may be further bounded by an internal surface of a lumen of the outer tube.

The cutting head may include helical threads, and at least one of the helical threads of the cutting head may include a proximal engagement tip engagable with a distal end of one of the helical threads of the harvesting member to facilitate rotation of the harvesting member. The outer tube may be tubular along its length to define a lumen.

At least one of the body of the cutting rod, the harvesting member, and the outer tube may be comprised at least in part of a flexible material. The flexible material may include at least one material selected from the group consisting of polyethylene (PE), polyvenylchloride (PVC), and polyurethane (PU). The flexible material may be reinforced with fibers selected from the group consisting of textile, metal, and plastic. The flexible material may include superelastic metal. One of the body of the cutting rod, the harvesting member, and the outer tube may be comprised at least in part of a first flexible material, and another of the body of the cutting rod, the harvesting member, and the outer tube may be comprised at least in part of a second flexible material different than the first flexible material.

At least one of the cutting rod, the harvesting member, and the outer tube may be a monolithic structure. At least one of the cutting rod, the harvesting member, and the outer tube may be a modular construct of two or more pieces. The instrument may further include a package in which the instrument is provided in an unassembled form. The instrument may further include a receptacle configured for attachment to a proximal end of the instrument for collecting harvested material. The instrument may further include a guidewire.

A second aspect of the present invention is an assembly including an intramedullary autograft harvesting instrument including a cutting rod having a body and a cutting head, a harvesting member configured to be disposed about the body of the cutting rod, and an outer tube configured to be disposed about the harvesting member. The outer tube is disposed about the harvesting member such that at least some threads of the harvesting member are in contact with an inner surface of a lumen of the outer tube. An outer surface of the body of the cutting rod is disposed within a lumen of the harvesting member such that at least a portion of the outer surface of the body and an inner surface of the lumen of the harvesting member are in contact.

In accordance with other embodiments of the second aspect, rotation between any two or more of the cutting rod, the harvesting member, and the outer tube may be permitted. Rotation may not be permitted between the cutting rod and the harvesting member. The assembly may further include a package in which the assembly is provided.

A third aspect of the present invention is a kit of surgical instruments including two or more intramedullary autograft harvesting instruments having different dimensions, wherein each intramedullary autograft harvesting instrument includes a cutting rod having a body and a cutting head, a harvesting member configured to be disposed about the body of the cutting rod, and an outer tube configured to be disposed about the harvesting member.

In accordance with other embodiments of the third aspect, the dimensions may include at least one of a diameter and a length of each instrument.

A fourth aspect of the present invention is a method of harvesting autograft tissue from an intramedullary canal including the steps of providing an intramedullary autograft harvesting instrument including a cutting rod having a body and a cutting head, a harvesting member configured to be disposed about the body of the cutting rod, and an outer tube configured to be disposed about the harvesting member, rotating the cutting rod and the harvesting member within the outer tube to ream bone tissue with the cutting head, and transporting harvested tissue away from the cutting head between the harvesting member and the outer tube.

In accordance with other embodiments of the fourth aspect, the method may further include step of connecting the cutting rod with a powered hand tool to transmit torque from the tool through the body to the cutting head. The step of rotating may include reaming cancellous bone tissue disposed within an intramedullary canal. The step of rotating may include maintaining the outer tube in an unrotated position relative to the harvesting member and the cutting rod. The step of rotating may include shaving cancellous bone into harvested material through use of the cutting head.

The step of transporting may include moving the harvested tissue proximally along flutes of threads of the cutting head and proximally along channels between threads of the harvesting member. The method may further include a step of collecting the harvested tissue in a receptacle at a proximal end of the instrument. The method may be performed without the use of saline solution. At least one of the steps of rotating and transporting may be performed with an axis of a proximal portion of the instrument at an angle with respect to an axis of a distal portion of the instrument.

A fifth aspect of the present invention is a method of using an instrument including the steps of providing an instrument including a cutting rod having a body and a cutting head, a harvesting member configured to be disposed about the body of the cutting rod, and an outer tube configured to be disposed about the harvesting member, and rotating the cutting rod and the harvesting member within the outer tube.

In accordance with other embodiments of the fifth aspect, the method may further include a step of transporting material away from the cutting head between the harvesting member and the outer tube. The step of transporting may include moving the material proximally along flutes of threads of the cutting head and proximally along channels between threads of the harvesting member. The method may further include a step of collecting the material in a receptacle at a proximal end of the instrument. At least one of the steps of rotating and transporting may be performed with an axis of a proximal portion of the instrument at an angle with respect to an axis of a distal portion of the instrument.

The method may further include a step of connecting the cutting rod with a powered hand tool to transmit torque from the tool through the body to the cutting head. The step of rotating may include maintaining the outer tube in an unrotated position relative to the harvesting member and the cutting rod. The method may be performed without the use of saline solution.

DETAILED DESCRIPTION

In describing the preferred embodiments of the subject illustrated and to be described with respect to the drawings, specific terminology will be used for the sake of clarity. However, the invention is not intended to be limited to any specific terms used herein, and it is to be understood that each specific term includes all technical equivalents that operate in a similar manner to accomplish similar purpose.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

FIGS. 1-9 show an intramedullary autograft harvesting instrument 100 in accordance with one embodiment of the present invention. Instrument 100 includes a flexible cutting rod 10, a flexible cannulated harvesting member 20 that fits over cutting rod 10, and a flexible outer tube 30 that covers harvesting member 20.

Figure 1:
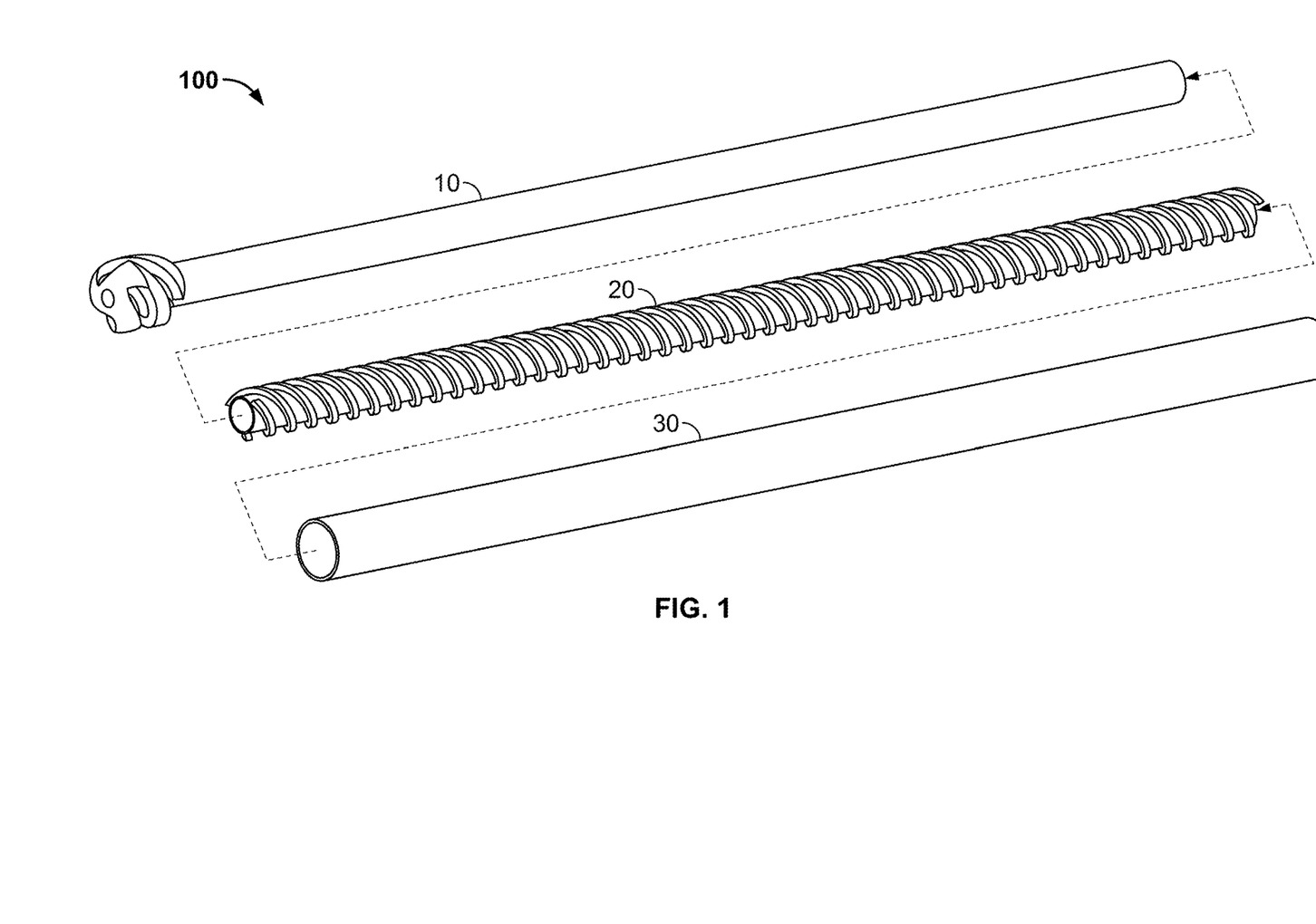
FIG. 1 is an exploded perspective view of an intramedullary autograft harvesting instrument in accordance with one embodiment of the present invention.
Figure 2:
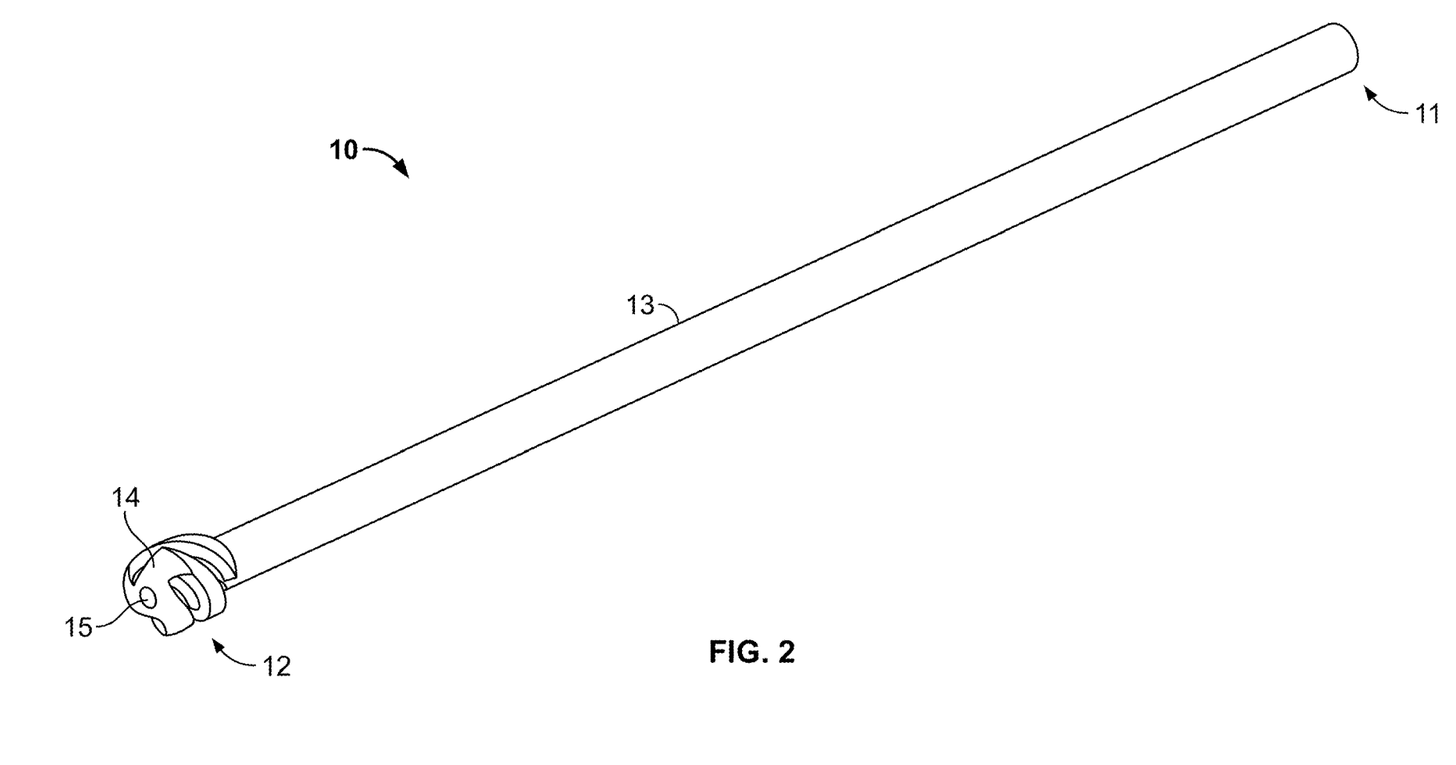
FIG. 2 is a perspective view of a cutting rod of the instrument shown in FIG. 1.
Figure 3:
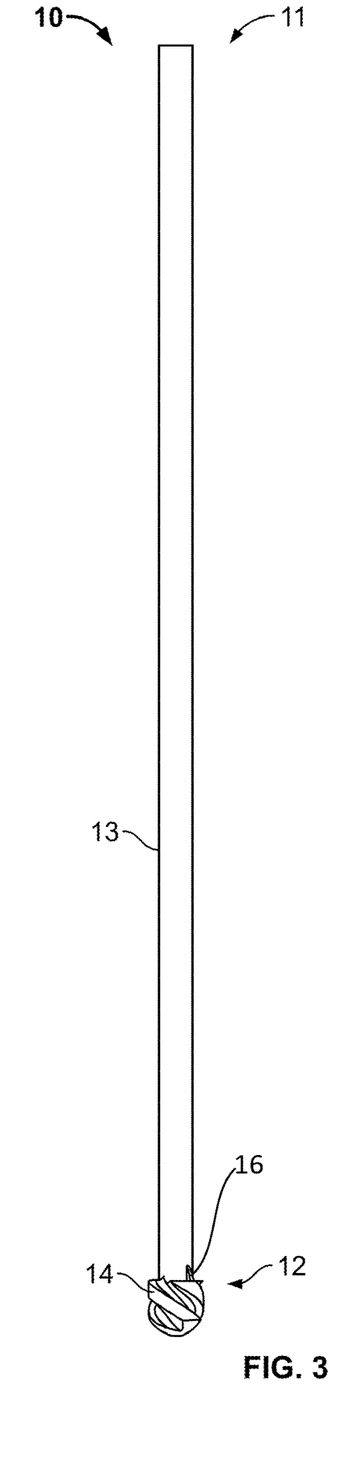
FIG. 3 is a front view of the cutting rod shown in FIG. 2.
Figure 4:
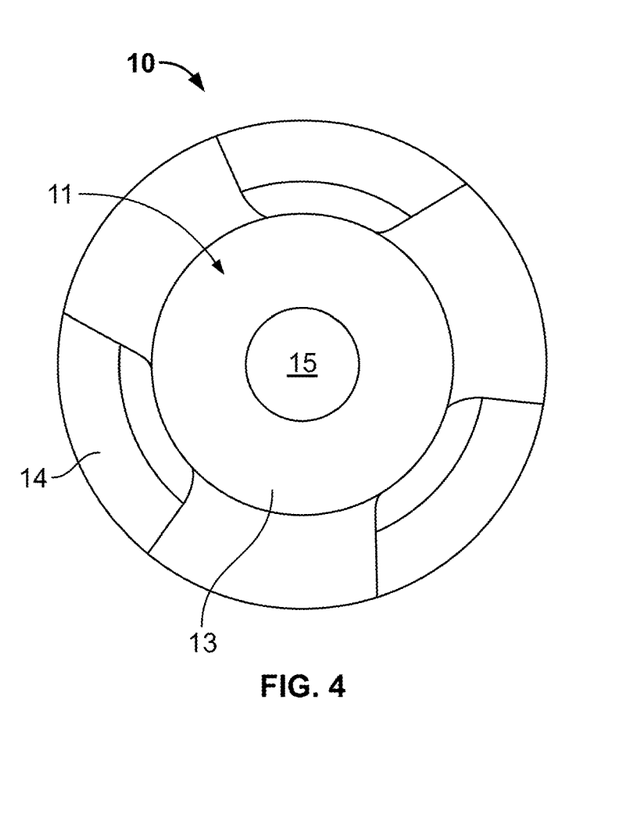
FIG. 4 is an elevational view of the proximal end of the cutting rod shown in FIG. 2.

Cutting rod 10 is shown in FIGS. 2-4 and includes a proximal end 11 and a distal end 12. Cutting rod 10 is comprised of a long, flexible body 13 extending between proximal end 11 and distal end 12 and a cutting head 14 connected with body 13 at distal end 12. Cutting rod 10 is cannulated with a bore 15 that extends through flexible body 13 and cutting head 14. Bore 15 can be disposed about a guidewire used during a surgical procedure. Also or in the alternative, bore 15 may be used to engage with a tool for rotating cutting rod 10.

Cutting head 14 is designed and configured to dislodge cancellous bone and to direct and transport it from the forward cutting area adjacent distal end 12 in a rearward direction toward proximal end 11 and, in the assembled instrument 100, harvesting member 20. Cutting head 14 is designed and configured to be able to dislodge the osseous tissue without the aided use of saline irrigation. Cutting head 14 can be configured in any manner that provides for bone reaming and removal of bone fragments and material, including being comprised of helical threads as shown in FIGS. 2-4. Other types of threads, cutting burr configurations, blades, or the like can be used. Cutting head 14 is of a diameter that is larger than that of body 13. The diameter of body 13 can be constant as shown in FIGS. 2-4. In other embodiments, the diameter of body 13 can vary along its length.

Figure 5:
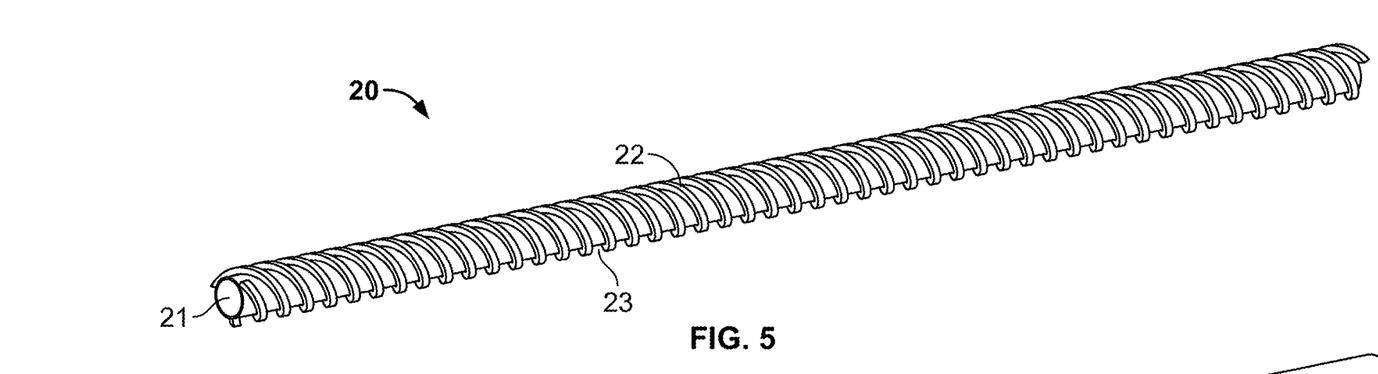
FIG. 5 is a perspective view of a harvesting member of the instrument shown in FIG. 1.

Shown in FIG. 5, harvesting member 20 is comprised of a flexible material and tubular shaped to define a lumen 21 in which cutting rod 10 can be disposed. Lumen 21 defines an inner diameter that fits around cutting rod 10. The outer surface of harvesting member 20 is configured and designed to transport harvested material away from distal end 12 of cutting rod 10 and proximally out of the intramedullary canal along harvesting member 20. Once the harvested material reaches the proximal end of the canal and harvesting member 20, it is collected in a receptacle. The outer surface of harvesting member 20 is comprised of one or more helical threads 22 that provide one or more helical channels 23 therebetween in which harvested material can be transported without the aid of irrigation. The width of channels 23 can be constant along their path or can vary. Different channels can have different widths. The imaginary outer surface on which the outermost portions of threads 22 are disposed can be a cylinder. The outer diameter of threads 22 can be constant or may vary.

Figure 6:
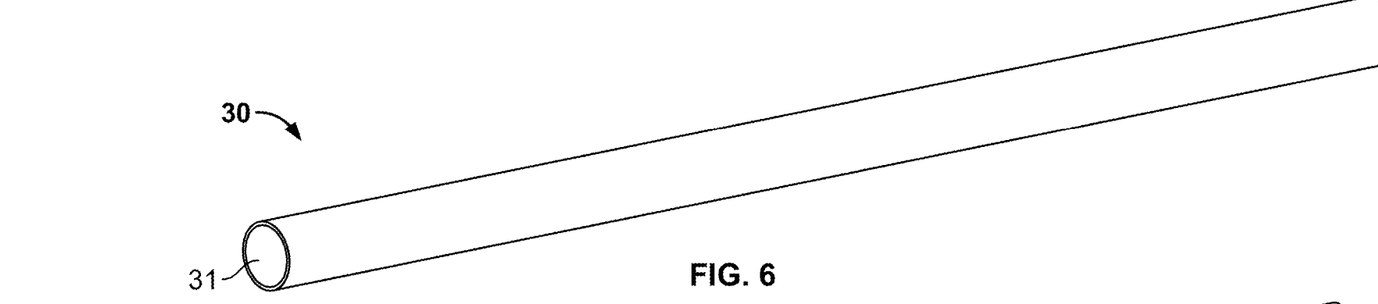
FIG. 6 is a perspective view of an outer tube of the instrument shown in FIG. 1.

Shown in FIG. 6, outer tube 30 is designed and configured to be flexible yet sufficiently stiff to be held by the user without impeding the movement of harvested material along the inner diameter of outer tube 30. Outer tube 30 also provides a lumen 31 having an internal surface whose inner diameter is designed to provide a pressure surface against the harvested material and harvesting member 20 to allow efficient transport of harvested material along harvesting member 20.

Each of the components of instrument 100 is comprised at least in part of a flexible material. While all materials inherently provide some measure of flexibility, it will be understood that flexible materials used in construction of the presently disclosed instruments allow for bending and movement among the components of the instruments to allow different configurations of the components to be achieved. In that regard, such flexible materials can be bent to a degree that a component of the instrument that is made of the flexible material can bend such that an axis along which a proximal portion of the component extends is angled with respect to an axis along which a distal portion of the component extends. That angle can be small, for example about 5 degrees, or can be much larger, for example about 90 degrees. Other angles that can be achieved are about 15 degrees, 30 degrees, and 45 degrees. Of course, other angles can be achieved based on the flexible material used and the configuration of the components of the instrument.

The flexible materials include, but are not limited to, polyethylene (PE), polyvenylchloride (PVC), and polyurethane (PU). These materials can be used for outer tube 30 and any other component of instrument 100. Since outer tube 30 is provided to transmit torque, it could be comprised at least in part of a material that is fiber reinforced. Such a material can be a polymer material such as one of those listed above or an equivalent material, with such polymer material having textile, metal, or other plastic fiber reinforcement. If not made from polymer material, outer tube 30 could also be made at least in part from superelastic metal, such as nitinol. Other components of the instrument could also be made from these fiber reinforced materials and/or superelastic metal. Materials of different flexibilities can be used to manufacture the different components. Body 13 of cutting rod 10 is comprised of a material that is sufficiently flexible to allow entry to the surgical site and into the intramedullary canal even if access is not permitted along the axis of the canal. Cutting head 14 of cutting rod 10 can be comprised of the same material as body 13, which allows some flexibility in cutting head 14 as well. However, the greater diameter of cutting head 14 compared with body 13 and added material thereof allow for cutting head 14 to maintain a rigid enough structure that can ream bone with which it comes into contact. Alternatively, cutting head 14 can be comprised of a material used for bone drilling, such as titanium or one or more other metals. Harvesting member 20 and outer tube 30 are also comprised of a material that is sufficiently flexible to allow entry to the surgical site and into the intramedullary canal even if access is not permitted along the axis of the canal. The material(s) comprising the components is such that one or more of the components or the entire instrument can be autoclaved or otherwise sterilized for reuse.

Each of the components of instrument 100 may be monolithic or can be modularly constructed in two or more pieces. For example, cutting head 14 can be manufactured separately from body 13 and later assembled. Threads 22 of harvesting member 20 can be provided separately from the tubular body of harvesting member 20 and later attached during assembly thereof.

Figure 7:
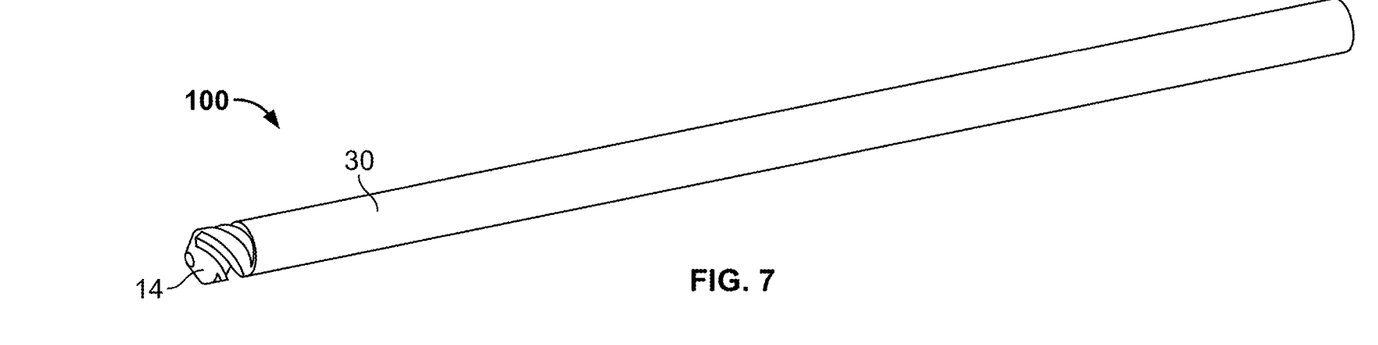
FIG. 7 is a perspective view of the assembled instrument shown in FIG. 1.
Figure 8:
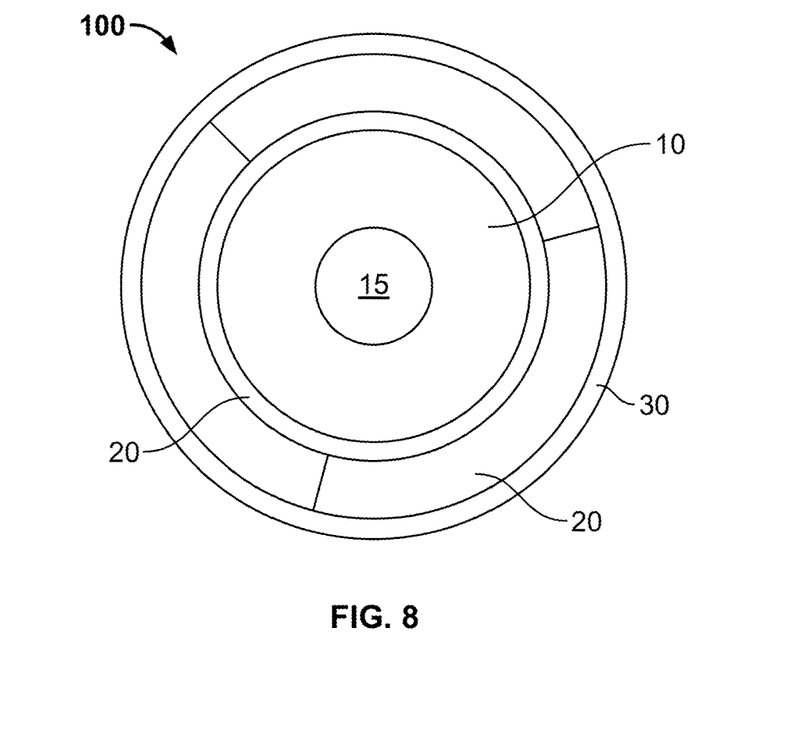
FIG. 8 is an elevational view of the proximal end of the assembled instrument shown in FIG. 1.
Figure 9:
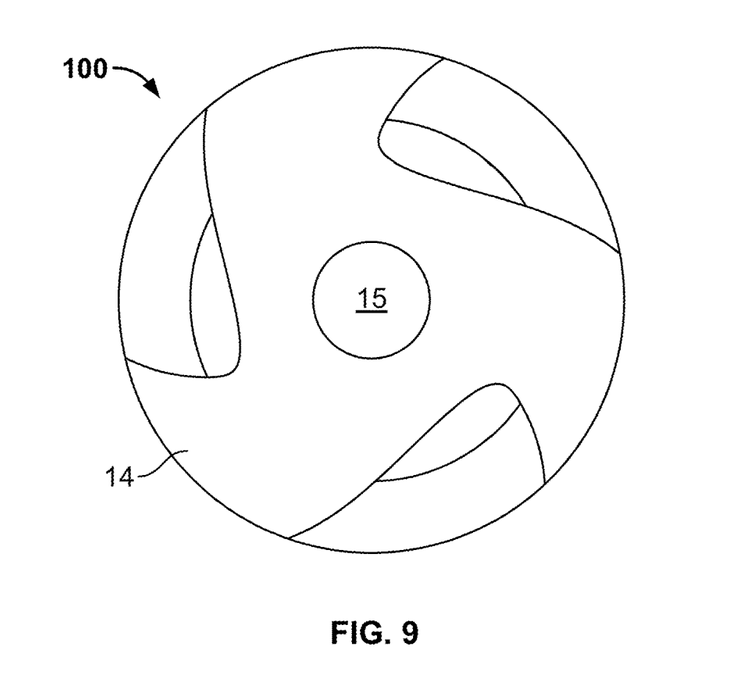
FIG. 9 is an elevational view of the distal end of the assembled instrument shown in FIG. 1.

When assembled as shown in FIGS. 7-9, instrument 100 includes outer tube 30 disposed about harvesting member 20 such that the exterior surface of threads 22 of harvesting member 20 are in close contact with the inner surface of lumen 31 of outer tube 30. The outer surface of body 13 of cutting rod 10 is disposed within lumen 21 of harvesting member 20 such that the outer surface of body 13 and the inner surface of lumen 21 are also in close contact. Rotation between any two of the components is permitted, although preferably cutting rod 10 and harvesting member 20 are connected such that they rotate about the longitudinal axis of instrument in unison without rotational movement therebetween. Preferably, the flexibility of the materials used in the construction of instrument 100 allow the assembled instrument 100 to flex and bend as a unit without substantially altering the configuration or operation of the localized bent portions of instrument 100. In FIG. 8, all components can be seen from the proximal end of instrument 100. In FIG. 9, the diameter of cutting head 14 is such that only cutting head 14 of cutting rod 10 can be seen from the distal end of instrument 100.

Assembly of instrument 100 can take place at the location of the surgical procedure by the user of the instrument 100, or else some or all of the components can be preassembled. A package can be provided to a user of the instrument containing the three separate components in an unassembled form. One or more of the components can be assembled with another in the package.

A kit of instruments can be provided with variations of instrument 100 in different dimensions, including different diameters and lengths. A kit of instruments can be provided with different lengths of the components of instrument 100 all having the same diameter. Other kits of instruments can be provided varying one or more of the dimensions and/or other configurations, such as the flexibility of the materials, of the components.

In use, cutting rod 10 can be connected with a powered hand tool, typically at proximal end 11, to transmit torque from the tool through flexible body 13 to cutting head 14. As instrument 100 is introduced into the intramedullary canal, cutting head 14 begins to contact the cancellous bone within the canal and the tool is powered to rotate cutting rod 10 and cutting head 14. Harvesting member 20 is also rotated at the same speed as cutting rod 10, though harvesting member 20 does not transmit torque to cutting head 14. Outer tube 30 can be held in a static position by the user such that harvesting member 20 and cutting rod 10 rotate therein.

As cutting head 14 encounters the cancellous bone of the canal, it shaves small portions of bone into harvested material. That material travels proximally along the flutes of the threads of cutting head 14. As the harvested material moves proximally past cutting head 14, it enters into channels 23 of harvesting member 20, thus proceeding along channels 23 between harvesting member 20 and outer tube 30. Continued rotation of cutting rod 10 and harvesting member 20 pushes more harvested material proximally until the harvested material exits channels 23 at a proximal end of the instrument and is captured in a receptacle. The configuration and operation of instrument 100 are such that the harvested material can be transported out of the reamed canal without the need for saline solution, thus preserving the integrity of the harvested material.

During the procedure, it is possible for cutting rod 10 to move distally further into the canal with respect to harvesting member 20. The space created between body 13 and the interior surface of the reamed canal can temporarily hold the harvested material as it is introduced into channels 23. In other configurations, cutting head 14 is flush with the distal end of harvesting member 20 during operation. Certain or all of the threads of cutting head 14 may include proximal engagement tips 16 that engage with the distal ends of one or more threads 22 of harvesting member 20 to facilitate at least in part, through connection of such elements, the rotation of harvesting member 20, particularly if the tool is only attached with body 13.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

INDUSTRIAL APPLICABILITY

The present invention enjoys wide industrial applicability including, but not limited to, devices and methods for harvesting autograft tissue.

The invention claimed is:

1. An intramedullary autograft harvesting instrument comprising:
   a cutting rod including a body and a cutting head with helical threads, the body having a first outer diameter and the cutting head having a second outer diameter, the second outer diameter being larger than the first outer diameter;
   a harvesting member slidably disposed about a portion of the body of the cutting rod; and
   an outer tube disposed about the harvesting member.

2. The instrument of claim 1, wherein the first outer diameter is constant along a length of the body of the cutting rod.

3. The instrument of claim 1, wherein the cutting head is disposed at a distal end of the cutting rod, the cutting head being configured to direct harvested material along the body of the cutting rod in a distal-proximal direction.

4. The instrument of claim 1, wherein the cutting rod is cannulated along its length to define a bore extending through the body and the cutting head.

5. The instrument of claim 1, wherein the outer surface of the harvesting member includes one or more helical threads defining one or more helical channels therebetween, such that the outer surface of the harvesting member is configured to transport harvested material away from a distal end of the cutting rod and in a proximal direction.

6. The instrument of claim 5, wherein the one or more helical channels are further bounded by an internal surface of a lumen of the outer tube.

7. The instrument of claim 1, wherein at least one of the helical threads of the cutting head terminates at a tip that is engagable with a distal end of one of the helical threads of the harvesting member to facilitate rotation of the cutting head and the harvesting member.

8. The instrument of claim 1, wherein at least one of the body of the cutting rod, the harvesting member, and the outer tube is comprised at least in part of a flexible material.

9. The instrument of claim 8, wherein the flexible material includes at least one material selected from the group consisting of polyethylene (PE), polyvenylchloride (PVC), and polyurethane (PU).

10. The instrument of claim 9, wherein the flexible material is reinforced with fibers selected from the group consisting of textile, metal, and plastic.

11. The instrument of claim 8, wherein the flexible material includes superelastic metal.

12. An assembly comprising:
    the intramedullary autograft harvesting instrument of claim 1,
    wherein the outer tube is disposed about the harvesting member such that at least some threads of the harvesting member are in contact with an inner surface of a lumen of the outer tube,
    wherein an outer surface of the body of the cutting rod is disposed within a lumen of the harvesting member such that at least a portion of the outer surface of the body and an inner surface of the lumen of the harvesting member are in contact.

13. The assembly of claim 12, wherein rotation between any two or more of the cutting rod, the harvesting member, and the outer tube is permitted.

14. The assembly of claim 12, wherein rotation is not permitted between the cutting rod and the harvesting member.

15. The instrument of claim 1, further comprising a receptacle configured for attachment to a proximal end of the instrument for collecting harvested material.

16. The instrument of claim 1, further comprising a guidewire.

17. An intramedullary autograft harvesting instrument comprising:
- a cutting rod including a body having a first outer diameter and a cutting head having a second outer diameter, the second outer diameter being larger than the first outer diameter;
- a harvesting member slidably disposed about a portion of the body of the cutting rod, the harvesting member including one or more helical threads that define one or more helical channels configured to transport harvested material away from a distal end of the cutting rod and in a proximal direction; and
- an outer tube disposed about the harvesting member.

* * * * *